(12) United States Patent
Harada

(10) Patent No.: US 8,896,940 B2
(45) Date of Patent: Nov. 25, 2014

(54) OBJECTIVE OPTICAL SYSTEM AND ENDOSCOPE USING SAME

(71) Applicant: FUJIFILM Corporation, Tokyo (JP)

(72) Inventor: Keisuke Harada, Saitama-ken (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 14/263,445

(22) Filed: Apr. 28, 2014

(65) Prior Publication Data
US 2014/0233112 A1    Aug. 21, 2014

Related U.S. Application Data

(63) Continuation of application No. PCT/JP2012/006971, filed on Oct. 31, 2012.

(30) Foreign Application Priority Data

Nov. 1, 2011    (JP) .................................. 2011-240149

(51) Int. Cl.
| | | |
|---|---|---|
| G02B 23/24 | (2006.01) | |
| G02B 9/34 | (2006.01) | |
| H04N 5/225 | (2006.01) | |
| G02B 13/04 | (2006.01) | |
| A61B 1/00 | (2006.01) | |

(52) U.S. Cl.
CPC *G02B 9/34* (2013.01); *G02B 13/04* (2013.01); *G02B 23/243* (2013.01); *A61B 1/00096* (2013.01); *A61B 1/00188* (2013.01)
USPC .......................................... 359/753; 348/345

(58) Field of Classification Search
CPC ........ G02B 23/243; G02B 9/34; G02B 13/04; A61B 1/00096; A61B 1/00188; H04N 2005/2255; H04N 5/225

USPC ........... 348/345; 359/660, 749, 752, 753, 781
See application file for complete search history.

(56) References Cited

U.S. PATENT DOCUMENTS

| | | | |
|---|---|---|---|
| 6,994,668 B2 | 2/2006 | Miyano | |
| 2008/0249367 A1 | 10/2008 | Miyano | |
| 2009/0086017 A1 | 4/2009 | Miyano | |
| 2014/0233113 A1* | 8/2014 | Harada et al. ................. | 359/781 |
| 2014/0233114 A1* | 8/2014 | Harada et al. ................. | 359/781 |

FOREIGN PATENT DOCUMENTS

| | | |
|---|---|---|
| JP | 10-111454 | 4/1998 |
| JP | 2004-145256 | 5/2004 |

(Continued)

OTHER PUBLICATIONS

International Search Report, PCT/JP2012/006971, Feb. 26, 2013.

*Primary Examiner* — David N Spector
(74) *Attorney, Agent, or Firm* — Young & Thompson

(57) ABSTRACT

The angle of view of an objective optical system is widened, while suppressing generation of lateral chromatic aberration. An objective optical system includes: a first lens group having a negative power; an aperture stop; and a second lens group having a positive power, in this order from an object side. The first lens group includes a negative single first lens, and a cemented lens formed by cementing a positive lens and a negative lens together, provided in this order from the object side. The second lens group includes a positive single fourth lens, and a cemented lens formed by cementing a positive lens and a negative lens together, provided in this order from the object side. The objective optical system satisfies Conditional Formula (1): $15.0 < vd(RN) < 18.6$, wherein $vd(RN)$ is the Abbe's number of the negative lens in the cemented lens within the second lens group with respect to the d line.

20 Claims, 13 Drawing Sheets

EXAMPLE 1

(56) References Cited

FOREIGN PATENT DOCUMENTS

| | | |
|---|---|---|
| JP | 2004-205779 | 7/2004 |
| JP | 2006-243092 | 9/2006 |
| JP | 2008-257108 | 10/2008 |
| JP | 2008-257109 | 10/2008 |
| JP | 2009-080413 | 4/2009 |
| JP | 2011-034106 | 2/2011 |
| JP | 2011-145315 | 7/2011 |
| JP | 2012-230434 | 11/2012 |
| JP | 2013-003267 | 1/2013 |

* cited by examiner

EXAMPLE 1

EXAMPLE 2

EXAMPLE 3

FIG.5 EXAMPLE 4
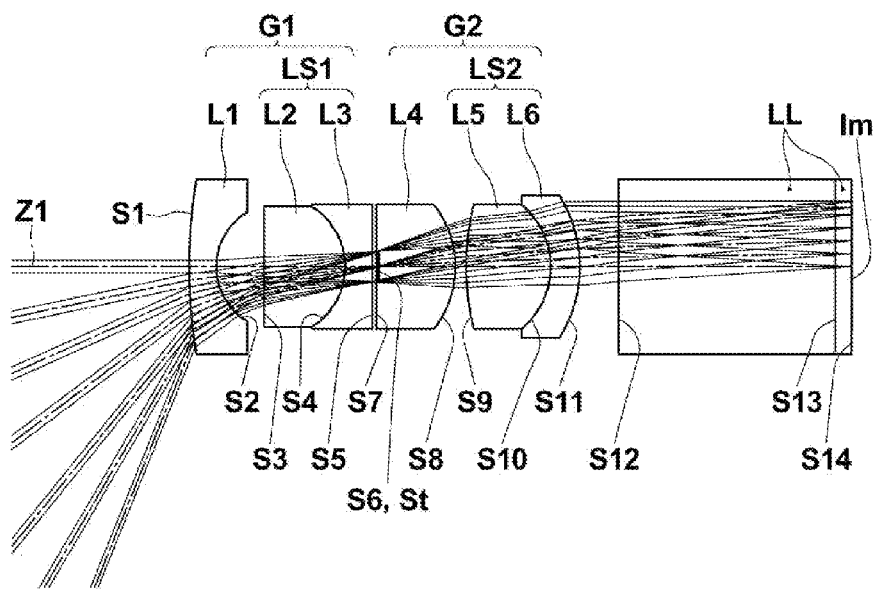
FIG.6 EXAMPLE 5
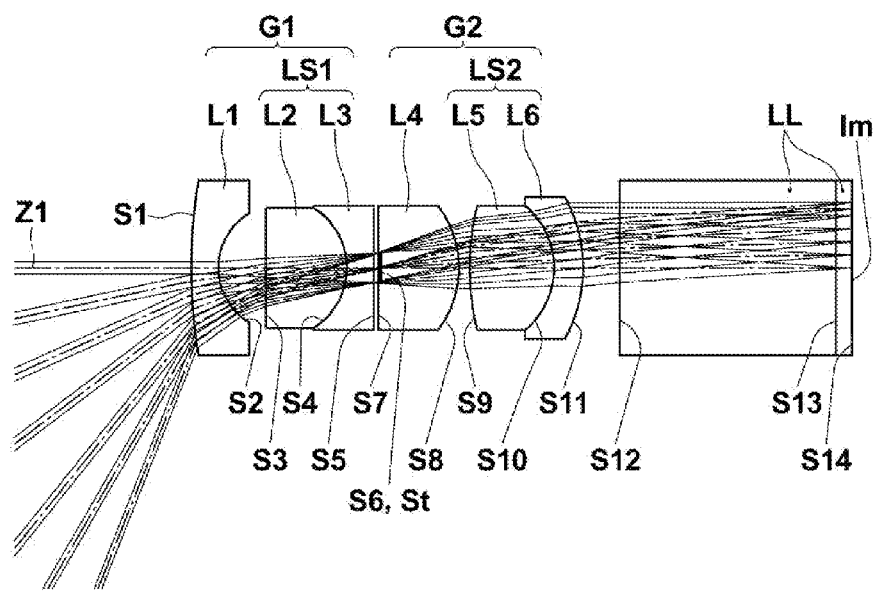

FIG.7  EXAMPLE 6
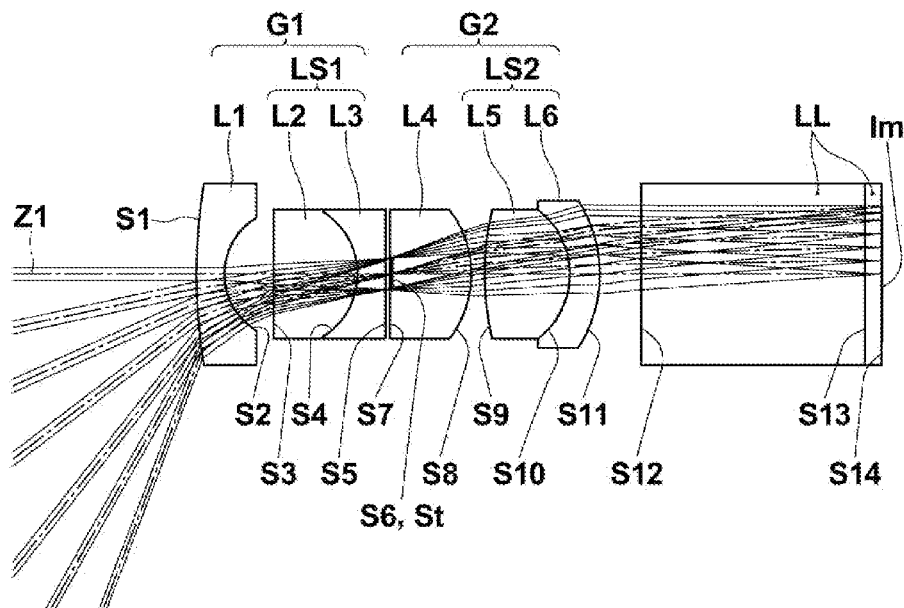
FIG.8  EXAMPLE 7
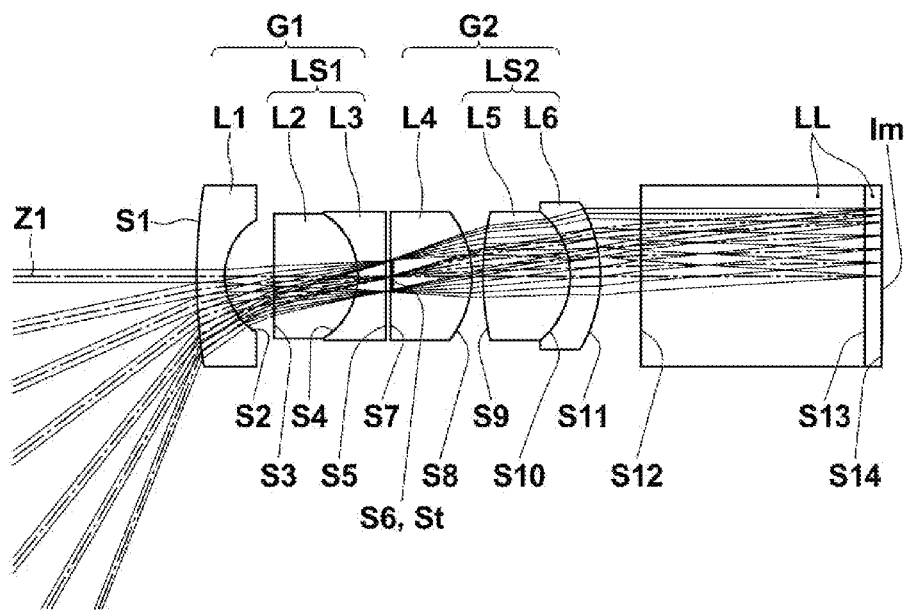

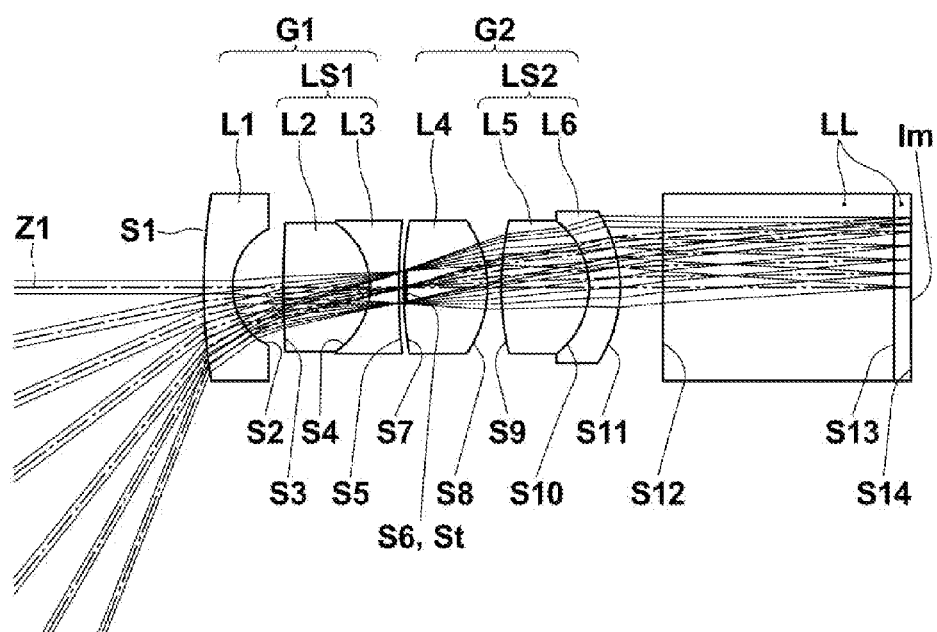
FIG.9   EXAMPLE 8

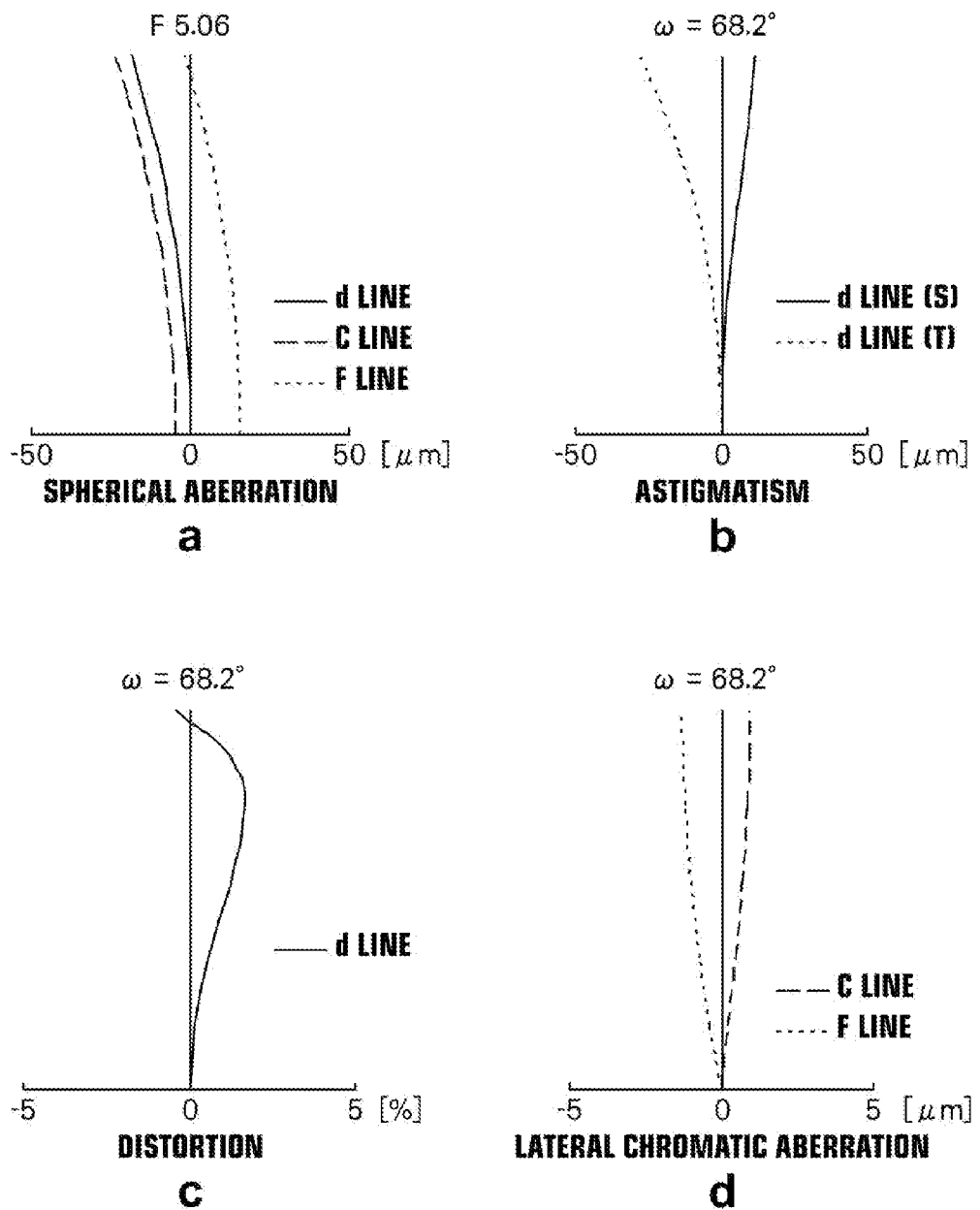

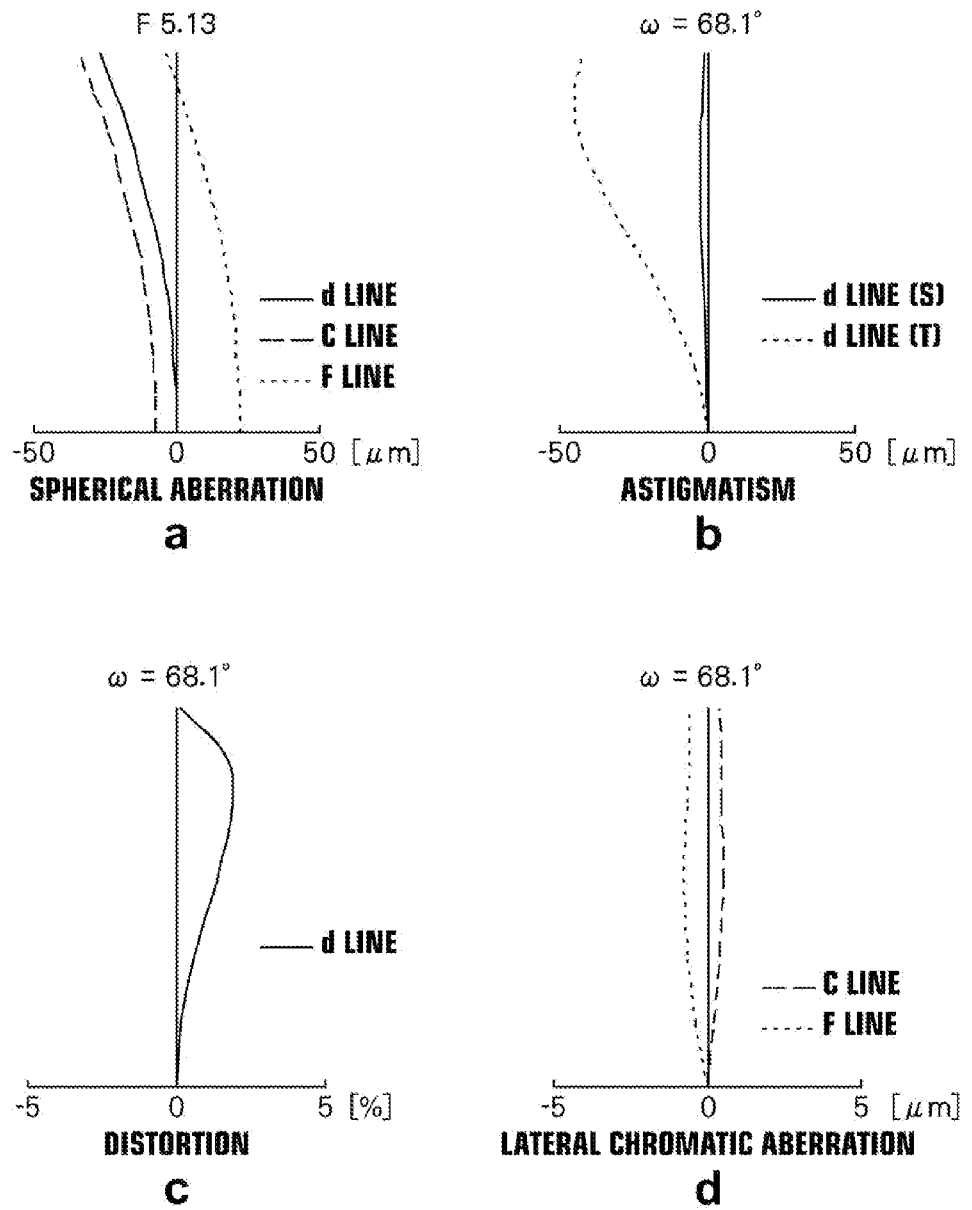

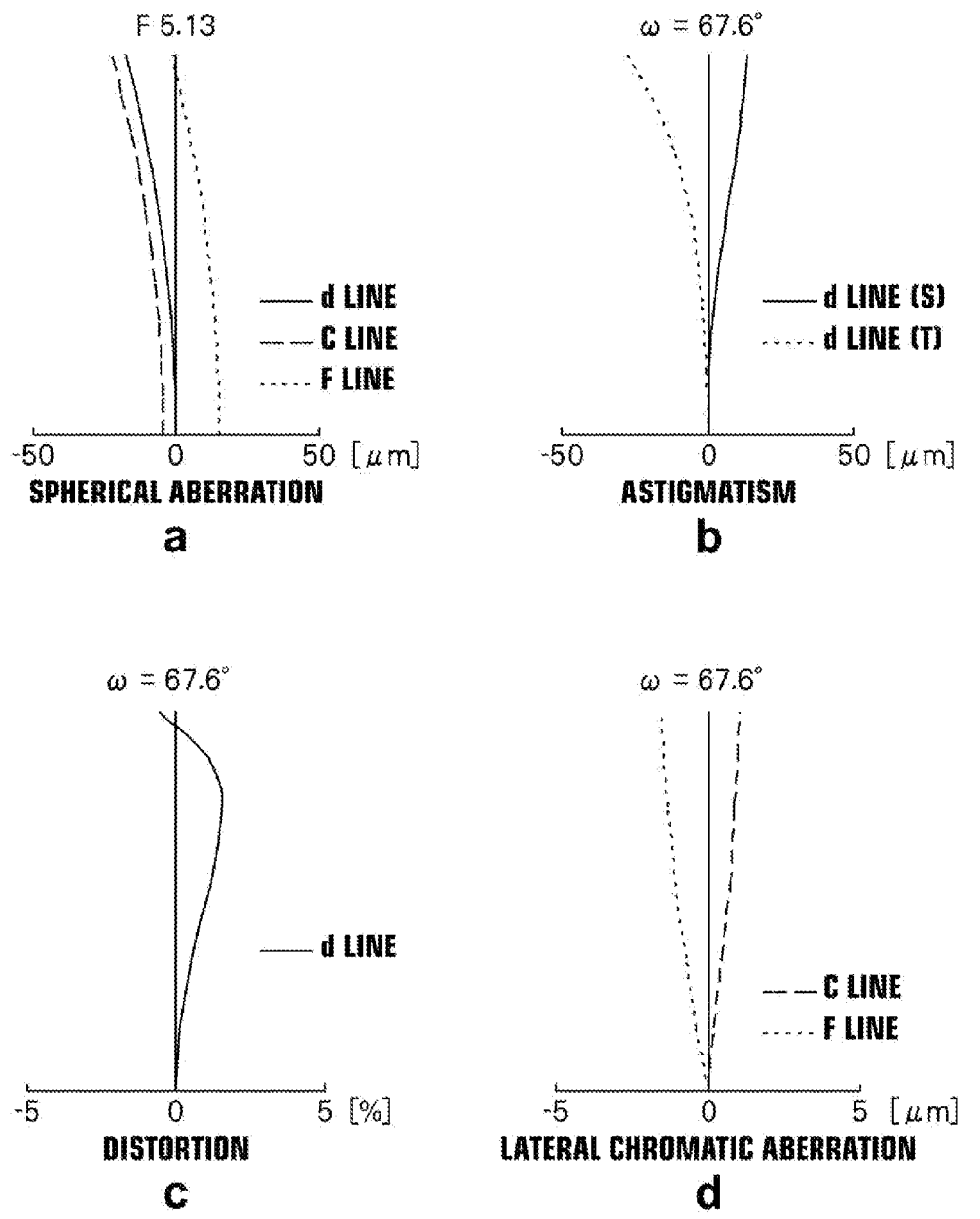

FIG.14
EXAMPLE 5
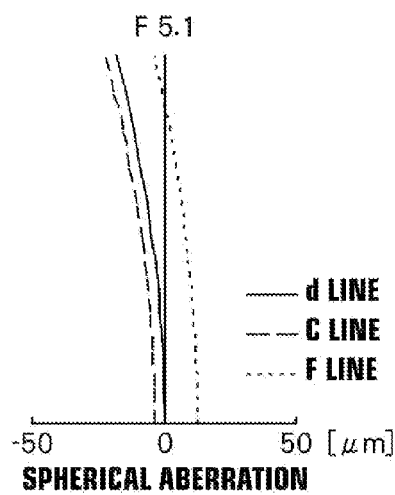
a
SPHERICAL ABERRATION
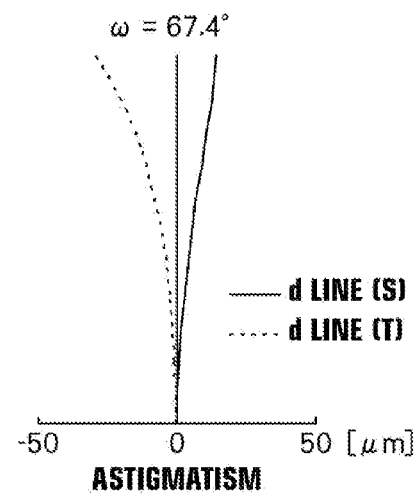
b
ASTIGMATISM
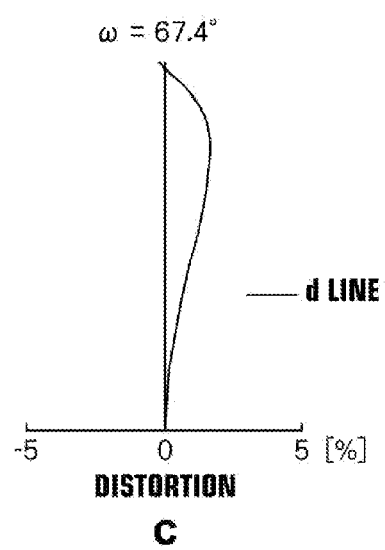
c
DISTORTION
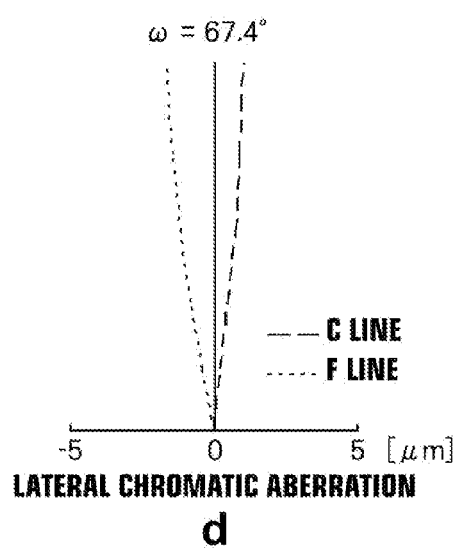
d
LATERAL CHROMATIC ABERRATION

FIG.15
EXAMPLE 6
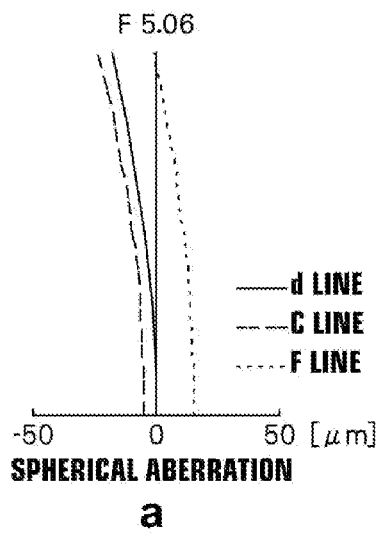
a
SPHERICAL ABERRATION
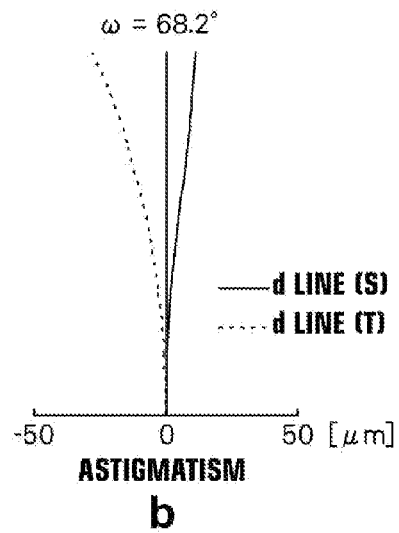
b
ASTIGMATISM
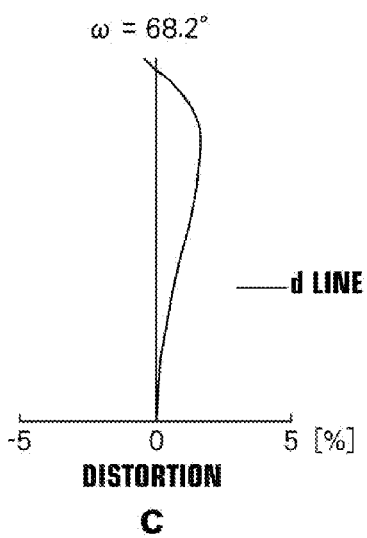
c
DISTORTION
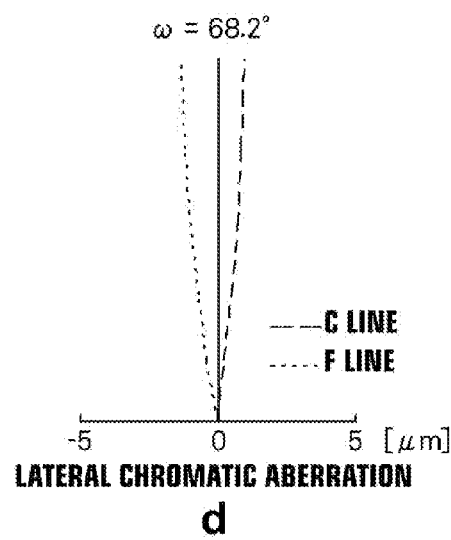
d
LATERAL CHROMATIC ABERRATION

OBJECTIVE OPTICAL SYSTEM AND ENDOSCOPE USING SAME

TECHNICAL FIELD

The present invention is related to an objective optical system having a first lens group and a second lens group, with an aperture stop interposed therebetween. The present invention is also related to an endoscope that employs such an objective optical system.

DESCRIPTION OF THE RELATED ART

Conventionally, there are cases in which lateral chromatic aberration of an objective optical system of an endoscope is not sufficiently corrected during diagnosis of the interior of a body cavity using the endoscope, resulting in color bleeding being generated in peripheral portions and diseased portions becoming difficult to observe. Correction of the lateral chromatic aberration is performed by an achromatizing cemented lens provided at a position remote from an aperture stop of the objective optical system of the endoscope. Lenses, formed by a high dispersion (low Abbe's number) material, having a negative power that constitute an achromatizing cemented lens provided more toward the image side than an aperture stop are known (refer to Japanese Unexamined Patent Publication Nos. 2008-257108, 2008-257109, and 2004-205779).

In such an objective optical system for an endoscope, if the powers of lenses provided more toward the object side than an aperture stop are determined in order to achieve widening of the angle of view, it will become difficult to suppress various aberrations. Therefore, objective optical systems that prioritize correction of aberrations over widening of the angle of view, by imparting a cemented lens provided more toward the object side than an aperture stop with a positive power are known (refer to Examples 1, 2, 3, and 4 of Japanese Unexamined Patent Publication No. 2004-205779). In addition, objective optical systems that prioritize widening of the angle of view over correction of aberrations, by imparting a cemented lens provided more toward the object side than an aperture stop with a negative power are known (refer to Example 5 of Japanese Unexamined Patent Publication No. 2008-257108 and Example 6 of Japanese Unexamined Patent Publication No. 2008-257109).

DISCLOSURE OF THE INVENTION

Recently, it is becoming possible to employ materials having even higher dispersion (low Abbe's number) as materials for lenses. For this reason, there is demand to obtain an objective optical system for an endoscope that sufficiently corrects lateral chromatic aberration while widening the angle of view, by employing such materials having high dispersion.

Note that this demand is not limited to objective optical systems for endoscopes, but also is present in the general field of objective optical systems as well.

The present invention has been developed in view of the foregoing circumstances. It is an object of the present invention to provide an objective optical system capable of suppressing the generation of lateral chromatic aberrations and widening the angle of view. It is another object of the present invention to provide an endoscope employing such an objective optical system.

A first objective optical system of the present invention comprises:
a first lens group having a negative refractive power;
an aperture stop; and
a second lens group having a positive refractive power, provided in this order from an object side;
the first lens group comprising a negative single lens and a cemented lens having a negative refractive power, formed by cementing a positive lens and a negative lens together, provided in this order from the object side;
the second lens group comprising a positive single lens and a cemented lens having a positive refractive power, formed by cementing a positive lens and a negative lens together, provided in this order from the object side; and
the objective optical system satisfying Conditional Formula (1) below:

$$15.0 < vd(RN) < 18.6 \tag{1}$$

wherein vd(RN) is the Abbe's number of the negative lens in the cemented lens within the second lens group with respect to the d line.

It is desirable for the first objective optical system of the present invention to satisfy Conditional Formula (1a): $16.0 < vd(RN) < 18.4$, and more desirable for the first objective optical system of the present invention to satisfy Conditional Formula (1b): $16.5 < vd(RN) < 18.2$.

A second objective optical system of the present invention comprises:
a first lens group having a negative refractive power;
an aperture stop; and
a second lens group having a positive refractive power, provided in this order from an object side;
the first lens group comprising a negative single lens and a cemented lens having a negative refractive power, formed by cementing a positive lens and a negative lens together, provided in this order from the object side;
the second lens group comprising a positive single lens and a cemented lens having a positive refractive power, formed by cementing a positive lens and a negative lens together, provided in this order from the object side; and the objective optical system satisfying Conditional Formula (2) below:

$$380 \leq vd(RN)/(ng-nF) < 1080 \tag{2}$$

wherein vd(RN) is the Abbe's number of the negative lens in the cemented lens within the second lens group with respect to the d line, ng is the refractive index of the negative lens in the cemented lens within the second lens group with respect to the g line (435.84 nm), and nF is the refractive index of the negative lens in the cemented lens within the second lens group with respect to the F line (486.13 nm).

It is desirable for the second objective optical system of the present invention to satisfy Conditional Formula (2a): $380 \leq vd(RN)/(ng-nF) < 600$, and more desirable for the second objective optical system of the present invention to satisfy Conditional Formula (2b): $380 \leq vd(RN)/(ng-nF) < 525$.

In the first and second objective optical systems of the present invention, the cemented lens within the first lens group may be formed by a positive lens having a convex surface toward the image side, and a negative lens, provided in this order from the object side.

In the first and second objective optical systems of the present invention, the cemented lens within the second lens group may be formed by a positive lens and a negative meniscus lens having a convex surface toward the image side, provided in this order from the object side. Alternatively, the cemented lens within the second lens group may be formed by a negative lens and a positive lens having a convex surface toward the image side, provided in this order from the object side.

It is desirable for the first and second objective optical systems of the present invention to satisfy Conditional Formula (3): vd(RP)+vd(RN)<79, more desirable for the first and second objective optical systems of the present invention to satisfy Conditional Formula (3a): 70<vd(RP)+vd(RN) <78.8, and even more desirable for the first and second objective optical systems of the present invention to satisfy Conditional Formula (3b): 75<vd(RP)+vd(RN)<78.5.

Here, vd(RP) is the Abbes number of the positive lens in the cemented lens within the second lens group with respect to the d line, and vd(RN) is the Abbes number of the negative lens in the cemented lens within the second lens group with respect to the d line.

It is desirable for the first and second objective optical systems of the present invention to satisfy Conditional Formula (4): 41.5<vd(RP)−vd(RN), more desirable for the first and second objective optical systems of the present invention to satisfy Conditional Formula (4a): 41.8<vd(RP)−vd(RN) <45.0, and even more desirable for the first and second objective optical systems of the present invention to satisfy Conditional Formula (4b): 42.0<vd(RP)−vd(RN)<44.0.

It is desirable for the first and second objective optical systems of the present invention to satisfy Conditional Formula (5): f1/f<−1.1, more desirable for the first and second objective optical systems of the present invention to satisfy Conditional Formula (5a): −1.5<f1/f<−1.1, and even more desirable for the first and second objective optical systems of the present invention to satisfy Conditional Formula (5b): −1.4<f1/f<−1.2.

Here, f1 is the focal length of the lens provided most toward the object side, and f is the focal length of the entire lens system.

It is desirable for the first and second objective optical systems of the present invention to satisfy Conditional Formula (6): 1.92<f2−6/f<3, more desirable for the first and second objective optical systems of the present invention to satisfy Conditional Formula (6a): 1.92<f2−6/f<2.5, and even more desirable for the first and second objective optical systems of the present invention to satisfy Conditional Formula (6b): 1.92<f2−6/f<2.2.

Here, f2−6 is the combined focal length of the lenses other than the lens provided most toward the object side, and f is the focal length of the entire lens system.

The first and second objective optical systems of the present invention may be employed as the objective optical system of an endoscope.

An endoscope of the present invention is equipped with one of the first and second objective optical systems of the present invention.

The first and second objective optical systems of the present invention substantially consist of two lens groups. Note that the expression "substantially consist of two lens groups" refers to cases including those in which the objective optical systems also include other components, such as lenses that practically do not have any power, optical elements other than lenses such as aperture stops and cover glasses, and mechanical components such as lens flanges, a lens barrel, an imaging device, and a blur correcting mechanism.

The first and second objective optical systems of the present invention substantially consist of six lenses. Note that the expression "substantially consist of six lenses" refers to cases including those in which the objective optical systems also include other components, such as lenses that practically do not have any power, optical elements other than lenses such as aperture stops and cover glasses, and mechanical components such as lens flanges, a lens barrel, an imaging device, and a blur correcting mechanism.

As described above, the first and second objective optical systems of the present invention may be constituted only by two lens groups and six lenses. Alternatively, the first and second objective optical systems of the present invention may also include lenses that practically do not have any power and optical elements other than lenses, in addition to the two lens groups and the six lenses. Note that with respect to the number of lenses in cases that cemented lenses are included, cemented lenses formed by cementing n lenses together will be counted as n lenses.

A single lens refers to one lens. That is, the expression "single lens" refers to an individual lens which is not cemented to another lens.

In the case that aspherical surfaces are employed in the objective optical systems of the present invention, the convexities and concavities of the aspherical surfaces, the signs of refractive powers, and the radii of curvature of the aspherical surfaces will be defined as those in the paraxial regions thereof.

In the first objective optical system of the present invention and the endoscope that employs this objective optical system, the first lens group having the negative refractive power, the aperture stop, and the second lens group having the positive refractive power are provided in this order from the object side. The first lens group is provided with the negative single lens and the cemented lens having the negative refractive power, formed by cementing the positive lens and the negative lens together, in this order from the object side. The second lens group is provided with the positive single lens and the cemented lens having the positive refractive power, formed by cementing the positive lens and the negative lens together, in this order from the object side. Further, the first objective optical system of the present invention is configured to satisfy Conditional Formula (1): 15.0<vd(RN)<18.6. Therefore, the angle of view can be widened while suppressing generation of lateral chromatic aberration.

Here, Conditional Formula (1) defines the Abbe's number of the negative lens in the cemented lens within the second lens group. Lateral chromatic aberration can be favorably corrected, by configuring the first objective optical system to satisfy Conditional Formula (1). That is, lateral chromatic aberration is prominently generated at positions remote from the aperture stop in the direction of the optical axis, at which the height of light rays is high. The cemented lens within the second lens group is provided at a position remote from the aperture stop in the direction of the optical axis with the positive single lens interposed therebetween. Therefore, lateral chromatic aberration can be favorably corrected by adjusting achromatization (adjusting the Abbe's number) using the negative lens within the cemented lens. Note that if the first objective optical system is configured such that the value of vd(RN) is greater than the upper limit defined in Conditional Formula (1), correction of lateral chromatic aberration will be insufficient. Meanwhile, if the first objective optical system is configured such that the value of vd(RN) is less than the lower limit defined in Conditional Formula (1), correction of longitudinal chromatic aberration will be insufficient.

In the second objective optical system of the present invention and the endoscope that employs this objective optical system, the first lens group having the negative refractive power, the aperture stop, and the second lens group having the positive refractive power are provided in this order from the object side. The first lens group is provided with the negative single lens and the cemented lens having the negative refractive power, formed by cementing the positive lens and the negative lens together, in this order from the object side. The second lens group is provided with the positive single lens and the cemented lens having the positive refractive power, formed by cementing the positive lens and the negative lens together, in this order from the object side. Further, the second objective optical system of the present invention is configured to satisfy Conditional Formula (2): 380≤vd(RN)/(ng−nF) <1080. Therefore, the angle of view can be widened while suppressing generation of lateral chromatic aberration. That is, lateral chromatic aberration is prominently generated at positions remote from the aperture stop in the direction of the optical axis, at which the height of light rays is high. The cemented lens within the second lens group is provided at a position remote from the aperture stop in the direction of the optical axis with the positive single lens interposed therebetween. Therefore, lateral chromatic aberration can be favorably corrected by adjusting achromatization (adjusting the Abbe's number) using the negative lens within the cemented lens.

Here, Conditional Formula (2) defines the ratio of the Abbe's number and partial dispersion, and is a conditional formula that restricts the selection range of lens materials to those having small Abbe's numbers. Lateral chromatic aberration can be favorably corrected, by configuring the second objective optical system to satisfy Conditional Formula (2).

Note that if the second objective optical system is configured such that the value of vd(RN)/(ng−nf) is greater than the upper limit defined in Conditional Formula (2), correction of lateral chromatic aberration will be insufficient. Meanwhile, if the second objective optical system is configured such that the value of vd(RN)/(ng−nf) is less than the lower limit defined in Conditional Formula (2), correction of longitudinal chromatic aberration will be insufficient.

According to the first and second objective optical systems of the present invention, optimized design can be achieved by selecting materials having the lowest Abbe's numbers from among high dispersion lens materials. In addition, the angle of view is widened by imparting a negative power to the cemented lens within the first lens group. Thereby, the angle of view can be widened while favorably correcting lateral chromatic aberration.

BRIEF DESCRIPTION OF THE DRAWINGS

FIG. 5 is a sectional diagram that illustrates the schematic configuration of an objective optical system of Example 4 along with the paths of light rays.

FIG. 6 is a sectional diagram that illustrates the schematic configuration of an objective optical system of Example 5 along with the paths of light rays.

FIG. 7 is a sectional diagram that illustrates the schematic configuration of an objective optical system of Example 6 along with the paths of light rays.

FIG. 8 is a sectional diagram that illustrates the schematic configuration of an objective optical system of Example 7 along with the paths of light rays.

FIG. 9 is a sectional diagram that illustrates the schematic configuration of an objective optical system of Example 8 along with the paths of light rays.

FIG. 10 is collection of diagrams that illustrate aberrations of the objective optical system of Example 1.

FIG. 11 is collection of diagrams that illustrate aberrations of the objective optical system of Example 2.

FIG. 12 is collection of diagrams that illustrate aberrations of the objective optical system of Example 3.

FIG. 14 is collection of diagrams that illustrate aberrations of the objective optical system of Example 5.

FIG. 15 is collection of diagrams that illustrate aberrations of the objective optical system of Example 6.

DESCRIPTION OF THE PREFERRED EMBODIMENTS

Hereinafter, objective optical systems of the present invention and endoscopes that employ the objective optical systems will be described with reference to the attached drawings.

Figure 1:
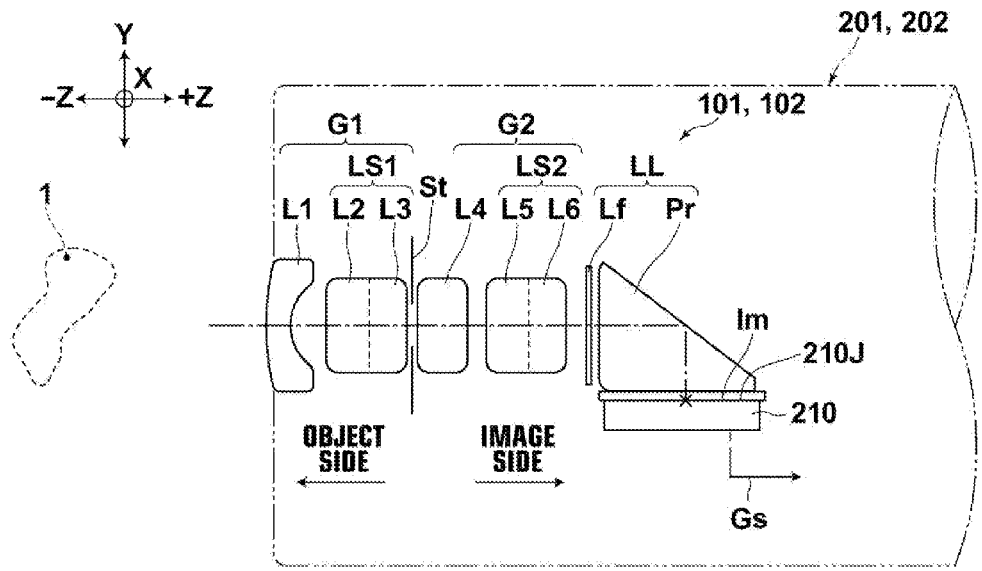
FIG. 1 is a sectional diagram that schematically illustrates common configurations of an endoscope equipped with an objective optical system according to a first embodiment of the present invention and an endoscope equipped with an objective optical system according to a second embodiment of the present invention.

FIG. 1 is a sectional diagram that schematically illustrates the common structures among an endoscope equipped with an objective optical system according to a first embodiment of the present invention and an endoscope equipped with an objective optical system according to a second embodiment of the present invention. Note that arrows X, Y, and Z in FIG. 1 indicate three directions which are perpendicular to each other, and the arrow Z indicates the same direction as that of an optical axis Z1. Note that the optical axis Z1 is an axis that matches a straight line that passes through the center of curvature of the surfaces of each of the lenses that constitute the objective optical system.

An endoscope 201 according to the first embodiment illustrated in FIG. 1 is equipped with an imaging device 210, which is a solid state imaging device such as a CCD and a CMOS, and an objective optical system 101 according to the first embodiment of the present invention. Note that FIG. 1 illustrates the distal end of a portion of the endoscope 201 to be inserted into a body cavity.

Light that propagates along the optical axis Z1, which is determined with respect to the single focus objective optical system 101 is deflected 90 degrees in a direction toward the imaging device 210 by an optical path converting prism Pr. A light receiving surface 210J of the imaging device 210 is provided parallel with respect to the optical axis Z1.

The imaging device 210 converts an optical image Im that represents a subject 1, which passes through the single focus objective optical system 101 and is focused on the light receiving surface 210J, into electrical signals, and outputs image signals Gs that represent the optical image Similarly, an endoscope 202 according to the second embodiment illustrated in FIG. 1 is equipped with an imaging device 210, which is a solid state imaging device such as a CCD and a CMOS, and a single focus objective optical system 102 according to the second embodiment of the present invention.

In the case of the endoscope 202 of the second embodiment as well, the imaging device 210 converts an optical image Im that represents a subject 1, which passes through the single focus objective optical system 102 and is focused on the light receiving surface 210J, into electrical signals, and outputs image signals Gs that represent the optical image Im.

Note that the objective optical system 101 of the first embodiment and the objective optical system 102 of the second embodiment are not limited to use in endoscopes, and may be employed as an objective lens in other apparatuses.

The objective optical system 101 of the first embodiment and the objective optical system 102 of the second embodiment have common configurations in the arrangement of lenses and aperture stops, as well as the refractive powers of a portion of the lenses therein. The common configurations are that a first lens group G1 having a negative refractive power, an aperture stop St, and a second lens group G2 having a positive refractive power, are provided in this order from the object side (the side of the −Z direction in FIG. 1). The first lens group G1 is provided with a first lens L1, which is a single lens having a negative refractive power, and a cemented lens LS1 having a negative refractive power as a whole, formed by cementing a lens having a positive refractive power and a lens having a negative refractive power together, in this order from the object side. The second lens group G2 is provided with a fourth lens L4, which is a single lens having a positive refractive power, and a cemented lens LS2 having a positive refractive power as a whole, formed by cementing a lens having a positive refractive power and a lens having a negative refractive power together, in this order from the object side.

Note that the objective optical system 101 of the first embodiment is configured to satisfy Conditional Formula (1): $15.0<vd(RN)<18.6$, in addition to the common configuration described above. Here, vd(RN) is the Abbe's number of the negative lens in the cemented lens LS2 within the second lens group G2 with respect to the d line.

It is desirable for the objective optical system 101 of the first embodiment to satisfy Conditional Formula (1a): $16<vd(RN)<18.4$, and more desirable for the objective optical system 101 of the first embodiment to satisfy Conditional Formula (1b): $16.5<vd(RN)<18.2$.

In addition, the objective optical system 102 of the second embodiment is configured to satisfy Conditional Formula (2): $380 \leq vd(RN)/(ng-nF)<1080$, in addition to the common configuration described above. Here, ng is the refractive index of the negative lens in the cemented lens LS2 within the second lens group G2 with respect to the g line (435.84 nm), and nF is the refractive index of the negative lens in the cemented lens LS2 within the second lens group G2 with respect to the F line (486.13 nm).

It is desirable for the objective optical system 102 to satisfy Conditional Formula (2a): $380 \leq vd(RN)/(ng-nF)<600$, and more desirable for the objective optical system 102 to satisfy Conditional Formula (2b): $380 \leq vd(RN)/(ng-nF)<525$.

In the objective optical system 101 and the objective optical system 102, the cemented lens LS1 within the first lens group G1 may be formed by a second lens L2, which is a lens having a positive refractive power and a convex surface toward the image side (the +Z direction in FIG. 1), and a third lens L3, which is a lens having a negative refractive power, provided in this order from the object side. In the case that the second lens L2 has a convex surface toward the image side and a positive refractive power, the back focus will be sufficiently long. Thereby, insertion of optical elements LL having no power, such as the optical path converting prism Pr and a filter Lf into the optical path corresponding to the back focus will be facilitated.

In the objective optical system 101 and the objective optical system 102, the cemented lens LS2 within the second lens group G2 may be formed by a fifth lens L5 having a positive refractive power and a sixth lens L6, which is a meniscus lens having a negative refractive power and a convex surface toward the image side, provided in this order from the object side. By configuring the cemented lens LS2 in this manner, favorable telecentric properties can be obtained, and principal rays of light can be caused to enter the light receiving surface 210J of the imaging device 210 substantially perpendicularly.

Alternatively, in the objective optical system 101 and the objective optical system 102, the cemented lens LS2 within the second lens group G2 may be formed by a fifth lens L5 having a negative refractive power and a sixth lens L6 having a positive refractive power and a convex surface toward the image side, provided in this order from the object side. By configuring the cemented lens LS2 in this manner, favorable telecentric properties can be obtained as in the case described above, and principal rays of light can be caused to enter the light receiving surface 210J of the imaging device 210 substantially perpendicularly.

Further, it is desirable for the objective optical system 101 and the objective optical system 102 to satisfy Conditional Formula (3) $vd(RP)+vd(RN)<79$, more desirable for the objective optical system 101 and the objective optical system 102 to satisfy Conditional Formula (3a) $70<vd(RP)+vd(RN)<78.8$, and even more desirable for the objective optical system 101 and the objective optical system 102 to satisfy Conditional Formula (3b): $75<vd(RP)+vd(RN)<78.5$. Here, vd(RP) is the Abbes number of the positive lens in the cemented lens LS2 within the second lens group G2 with respect to the d line, and vd(RN) is the Abbes number of the negative lens in the cemented lens LS2 within the second lens group G2 with respect to the d line.

Conditional Formula (3) is a conditional formula that restricts the selection range of lens materials to those having small Abbe's numbers.

Favorable correction of lateral chromatic aberration becomes possible if Conditional Formula (3) is satisfied.

Here, if the value of vd(RP)+vd(RN) is greater than the upper limit defined in Conditional Formula (3), correction of lateral chromatic aberration will be insufficient. Meanwhile, if the value of vd(RP)+vd(RN) is less than the lower limit defined in Conditional Formula (3), correction of longitudinal chromatic aberration will be insufficient. The operational effects of Conditional Formulae (3a) and (3b) are the same as those described above. It is desirable for the objective optical system 101 and the objective optical system 102 to satisfy Conditional Formula (4): $41.5<vd(RP)-vd(RN)$, more desirable for the objective optical system 101 and the objective optical system 102 to satisfy Conditional Formula (4a): $41.8<vd(RP)-vd(RN)<45.0$, and even more desirable for the objective optical system 101 and the objective optical system 102 to satisfy Conditional Formula (4b): $42.0<vd(RP)-vd(RN)<44.0$.

Conditional Formula (4) is also a conditional formula that restricts the selection range of lens materials to those having small Abbe's numbers, similar to Conditional Formula (3). Favorable correction of lateral chromatic aberration becomes possible if Conditional Formula (4) is satisfied.

Here, if the value of vd(RP)−vd(RN) is greater than the upper limit defined in Conditional Formula (4), correction of lateral chromatic aberration will be insufficient. Meanwhile, if the value of vd(RP)−vd(RN) is less than the lower limit defined in Conditional Formula (4), the range of selection of appropriate glass materials will become narrow, and correction of longitudinal chromatic aberration will be insufficient. The operational effects of Conditional Formulae (4a) and (4b) are the same as those described above.

In addition, it is desirable for the objective optical system 101 and the objective optical system 102 to satisfy Conditional Formula (5): f1/f<−1.1, more desirable for the objective optical system 101 and the objective optical system 102 to satisfy Conditional Formula (5a): −1.5<f1/f<−1.1, and even more desirable for the objective optical system 101 and the objective optical system 102 to satisfy Conditional Formula (5b): −1.4<f1/f<−1.2. Here, f1 is the focal length of the lens provided most toward the object side, and f is the focal length of the entire lens system.

Widening of the angle of view to a range from 130 degrees to 140 degrees will become possible if Conditional Formula (5) is satisfied.

Here, if the value of f1/f is greater than the upper limit defined in Conditional Formula (5), the heights of rays of light that pass through the negative single lens provided most toward the object side will become high, although the angle of view can be increased. Therefore, it will become necessary to increase the outer diameter of the first lens L1. Meanwhile, if the value of f1/f is less than the lower limit defined in Conditional Formula (5), the angel of view will decrease, and it will become difficult to achieve a desired widening of the angle of view in the objective optical systems 101 and 102. Note that the operational effects of Conditional Formulae (5a) and (5b) are the same as those described above.

In addition, it is desirable for the objective optical system 101 and the objective optical system 102 to satisfy Conditional Formula (6): 1.92<f2−6/f<3, more desirable for the objective optical system 100 to satisfy Conditional Formula (6a): 1.92<f2−6/f<2.5, and even more desirable for the objective optical system 100 to satisfy Conditional Formula (6b): 1.92<f2−6/f<2.2. Here, f2−6 is the combined focal length of the lenses other than the first lens L1 provided most toward the object side, and f is the focal length of the entire lens system. That is, f2−6 is the combined focal length of the second lens L2, the third lens L3, the fourth lens L4, the fifth lens L5, and the sixth lens L6.

If the value of f2−6/f is greater than the upper limit defined in Conditional Formula (6), the angle of view will become small, and it will become difficult to achieve a widening of the angle of view desired for the objective optical systems 101 and 102. Meanwhile, if the value of f2−6/f is less than the lower limit defined in Conditional Formula (6), the back focus will become short, and insertion of optical elements LL having no power, (for example, the optical path converting prism Pr and the filter Lf) into the optical path corresponding to the back focus will become difficult. Note that the operational effects of Conditional Formulae (6a) and (6b) are the same as those described above.

EXAMPLES

Next, Examples 1 through 8, which indicate data of specific numerical values of the objective optical system of the present invention, will be described with reference to FIGS. 2 through 9, FIGS. 10 through 17, Tables 1 through 8, and Table 9.

Note that reference numerals within FIGS. 2 through 9 that match the reference numerals in FIG. 1 that illustrates the objective optical systems 101 and 102 indicate corresponding constituent elements.

Example 1

Figure 2:
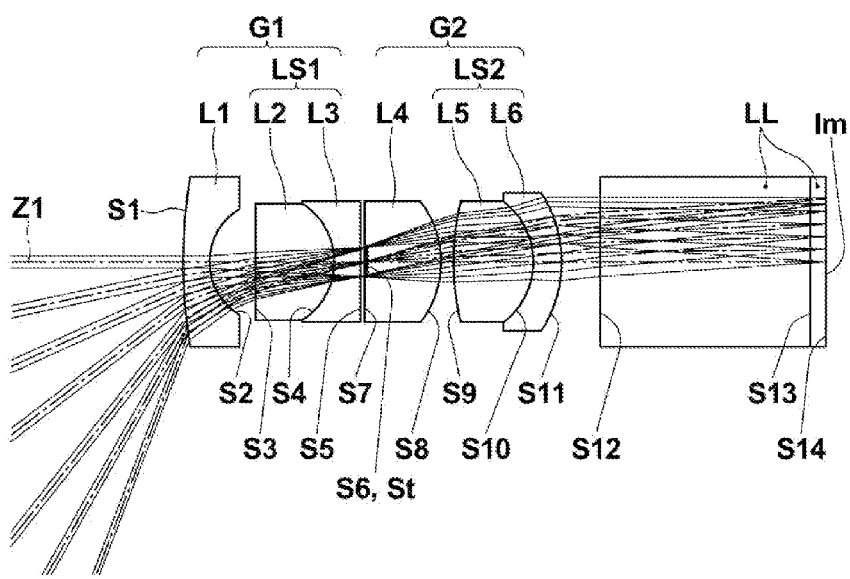
FIG. 2 is a sectional diagram that illustrates the schematic configuration of an objective optical system of Example 1 along with the paths of light rays.

FIG. 2 is a sectional diagram that illustrates the schematic configuration of an objective optical system of Example 1 along with the paths of light rays that pass through the objective optical system.

The objective optical system of Example 1 corresponds to both the first objective optical system and the second objective optical system described above, and is configured to of Conditional Formulae (1) through (6). A cemented lens LS2 within a second lens group G2 of the objective optical system of Example 1 differs from that of an objective optical system of Example 2 to be described later, in that the cemented lens LS2 is formed by a fifth lens L5 having a positive refractive power and a sixth lens L6, which is a meniscus lens having a negative refractive power and a convex surface toward the image side, provided in this order from the object side.

Table 1 shows lens data of the objective optical system of Example 1. In the lens data shown in Table 1, surface numbers Si (i=1, 2, 3, . . . ) are surface numbers that sequentially increase from the object side to the image side, with the surface provided most toward the object side designated as 1. Note that the lens data also include surface numbers of an aperture stop St, optical elements LL (for example, an optical path converting prism, a filter, etc.) that do not have any power, and an imaging surface on which the optical image Im is focused.

The symbol Ri in Table 1 indicates the radii of curvature of $i^{th}$ i=1, 2, 3, . . . ) surfaces. The symbol Di indicates the distances between $i^{th}$ surfaces and $i+1^{st}$ surfaces along the optical axis Z1. The numbers of the values indicated for the symbol Ri and the symbol Si correspond to the numbers of the symbol Si (i=1, 2, 3, . . . ) that indicate lens surfaces, the aperture stop, etc. Note that in Table 1, the units of measurement for the radii of curvature and the distances among surfaces are mm. The signs of the radii of curvature are positive in the case that surfaces are convex toward the object side, and negative in the case that surfaces are convex toward the image side.

The symbol Ndj in Table 1 indicates the refractive indices of $j^{th}$ (j=1, 2, 3, . . . ) optical elements with respect to the d line (wavelength: 587.6 nm), and vdj indicates the Abbe's numbers of $j^{th}$ optical elements (optical members) with respect to the d line. j is a number that sequentially increases from the object side to the image side, with the optical element most toward the object side designated as 1.

Note that it is possible for optical systems such as that described above to be proportionately enlarged or proportionately reduced and utilized. Therefore, objective optical systems in which the entirety of the aforementioned lens data is proportionately enlarged or proportionately reduced may be Examples of the present invention as well.

TABLE 1

Example 1: Lens Data

| Surface Number (i) | Radius of Curvature (Ri) | Distance (Di) | Ndj | vdj |
|---|---|---|---|---|
| 1 | 4.9998 | 0.25 | 1.88300 | 40.80 |
| 2 | 0.5800 | 0.44 | | |
| 3 | ∞ | 0.75 | 1.72825 | 28.50 |
| 4 | −0.6452 | 0.25 | 1.88300 | 40.80 |
| 5 | ∞ | 0.04 | | |
| 6 (Aperture Stop) | ∞ | 0.00 | | |
| 7 | ∞ | 0.73 | 1.51633 | 64.10 |
| 8 | −0.9258 | 0.12 | | |

TABLE 1-continued

Example 1: Lens Data

| Surface Number (i) | Radius of Curvature (Ri) | Distance (Di) | Ndj | vdj |
|---|---|---|---|---|
| 9 | 2.4390 | 0.76 | 1.62041 | 60.30 |
| 10 | −0.7143 | 0.27 | 2.10205 | 16.80 |
| 11 | −1.1886 | 0.37 | | |
| 12 | ∞ | 2.00 | 1.55920 | 53.90 |
| 13 | ∞ | 0.15 | 1.51633 | 64.10 |
| 14 | ∞ | 0.00 | | |

FIG. 10 is a collection of diagrams that illustrate aberrations regarding the objective optical system of Example 1. a of FIG. 10 illustrates spherical aberration, FIG. 10 illustrates astigmatism, FIG. 10 illustrates distortion, and FIG. 10 illustrates lateral chromatic aberration.

Note that in the diagram that illustrates astigmatism, the solid line indicates aberration in a sagittal direction, and the broken line indicates aberration in a tangential direction. In addition, "F5.06" shown above the diagram that illustrates spherical aberration indicates that the F number is 5.06. "ω=68.2°" shown above the diagrams that illustrate other aberrations indicate that the half angle of view is 68.2°.

Further, values of the objective optical system of Example 1 that correspond to the equations and variables in each of the conditional formulae described above are shown in Table 9. The values of the equations and variables can be derived from the lens data shown in Table 1 and the like. Note that the focal lengths of the lenses corresponding to the variables within the equations, and the focal lengths of combinations of a plurality of lenses (combined focal lengths) are distinguished as positive and negative.

Table 9 also shows values of objective optical systems of Examples 2 through 8 to be described later that correspond to the equations and variables in each of the conditional formulae described above.

As can be understood from the above lens data and the like, the angle of view of the objective optical system of Example 1 can be widened while suppressing the generation of lateral chromatic aberration.

The manners in which FIG. 2 that illustrates the configuration, FIG. 10 that illustrates the aberrations, Table 1 that shows the lens data, and Table 9 related to the conditional formulae of the objective optical system of Example 1 are to be interpreted are the same as those for the figures and tables related to Examples 2 through 8 to be described later. Therefore, descriptions thereof will be omitted with respect to the Examples to be described later.

Example 2

Figure 3:
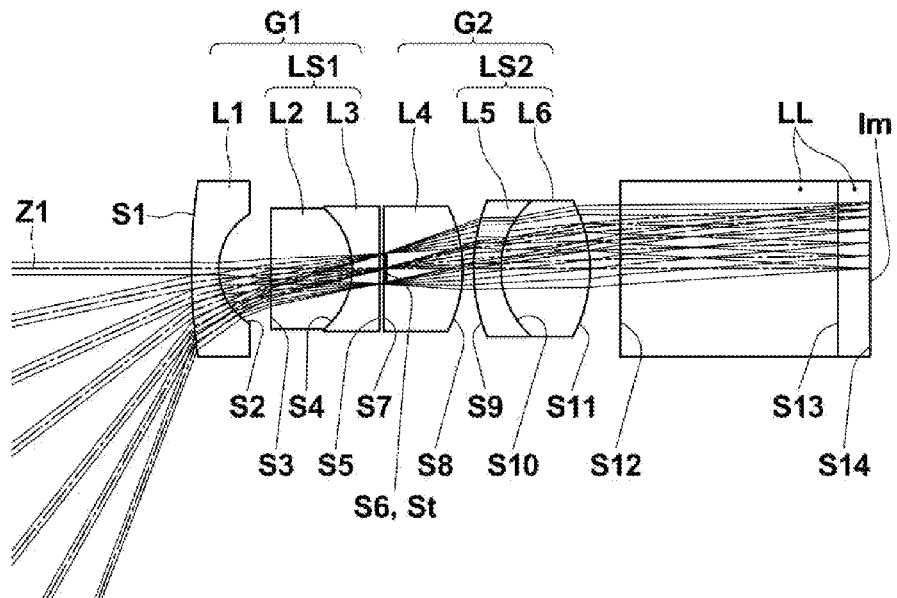
FIG. 3 is a sectional diagram that illustrates the schematic configuration of an objective optical system of Example 2 along with the paths of light rays.

FIG. 3 is a sectional diagram that illustrates the schematic configuration of an objective optical system of Example 2 along with the paths of light rays that pass through the objective optical system.

The objective optical system of Example 2 corresponds to both the first objective optical system and the second objective optical system described above, and is configured to satisfy all of Conditional Formulae (1) through (6). A cemented lens LS2 within a second lens group G2 of the objective optical system of Example 2 differs from that of the objective optical system of Example 1, in that the cemented lens LS2 is formed by a fifth lens L5 having a negative refractive power and a sixth lens L6, which is a lens having a positive refractive power and a convex surface toward the image side, provided in this order from the object side.

FIG. 11 is a collection of diagrams that illustrate aberrations of the objective optical system of Example 2.

Table 2 below shows lens data of the objective optical system of Example 2.

TABLE 2

Example 2: Lens Data

| Surface Number (i) | Radius of Curvature (Ri) | Distance (Di) | Ndj | vdj |
|---|---|---|---|---|
| 1 | 5.3203 | 0.25 | 1.88300 | 40.80 |
| 2 | 0.5800 | 0.48 | | |
| 3 | ∞ | 0.75 | 1.72825 | 28.50 |
| 4 | −0.7127 | 0.25 | 1.88300 | 40.80 |
| 5 | ∞ | 0.04 | | |
| 6 (Aperture Stop) | ∞ | 0.00 | | |
| 7 | ∞ | 0.73 | 1.51633 | 64.10 |
| 8 | −1.2431 | 0.10 | | |
| 9 | 1.6189 | 0.25 | 1.95906 | 17.50 |
| 10 | 0.8124 | 0.82 | 1.62041 | 60.30 |
| 11 | −1.3016 | 0.28 | | |
| 12 | ∞ | 2.00 | 1.55920 | 53.90 |
| 13 | ∞ | 0.30 | 1.51633 | 64.10 |
| 14 | ∞ | 0.00 | | |

As can be understood from the above lens data and the like, the angle of view of the objective optical system of Example 2 can be widened while suppressing the generation of lateral chromatic aberration.

Example 3

Figure 4:
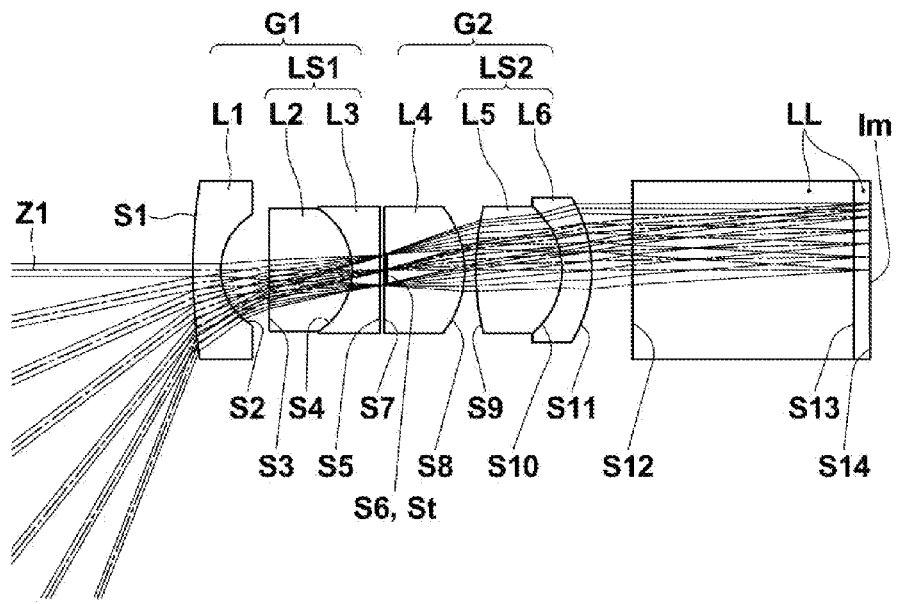
FIG. 4 is a sectional diagram that illustrates the schematic configuration of an objective optical system of Example 3 along with the paths of light rays.

FIG. 4 is a sectional diagram that illustrates the schematic configuration of an objective optical system of Example 3 along with the paths of light rays that pass through the objective optical system.

The objective optical system of Example 3 corresponds to both of the first objective optical system and the second objective optical system described above, and is configured to satisfy all of Conditional Formulae (1) through (6). A cemented lens LS2 within a second lens group G2 of the objective optical system of Example 3 is the same as that of Example 1. That is, the cemented lens LS2 is formed by a fifth lens L5 having a positive refractive power and a sixth lens L6, which is a meniscus lens having a negative refractive power and a convex surface toward the image side, provided in this order from the object side.

FIG. 12 is a collection of diagrams that illustrate aberrations of the objective optical system of Example 3.

Table 3 below shows lens data of the objective optical system of Example 3.

TABLE 3

Example 3: Lens Data

| Surface Number (i) | Radius of Curvature (Ri) | Distance (Di) | Ndj | vdj |
|---|---|---|---|---|
| 1 | 5.2535 | 0.25 | 1.88300 | 40.80 |
| 2 | 0.5800 | 0.44 | | |
| 3 | ∞ | 0.75 | 1.72825 | 28.50 |
| 4 | −0.6452 | 0.25 | 1.88300 | 40.80 |
| 5 | ∞ | 0.04 | | |
| 6 (Aperture Stop) | ∞ | 0.00 | | |
| 7 | ∞ | 0.73 | 1.51633 | 64.10 |
| 8 | −0.9202 | 0.10 | | |
| 9 | 2.3148 | 0.78 | 1.62041 | 60.30 |

TABLE 3-continued

Example 3: Lens Data

| Surface Number (i) | Radius of Curvature (Ri) | Distance (Di) | Ndj | vdj |
|---|---|---|---|---|
| 10 | −0.7407 | 0.27 | 2.10205 | 16.80 |
| 11 | −1.2428 | 0.37 | | |
| 12 | ∞ | 2.00 | 1.55920 | 53.90 |
| 13 | ∞ | 0.15 | 1.51633 | 64.10 |
| 14 | ∞ | 0.00 | | |

As can be understood from the above lens data and the like, the angle of view of the objective optical system of Example 3 can be widened while suppressing the generation of lateral chromatic aberration.

Example 4

FIG. 5 is a sectional diagram that illustrates the schematic configuration of an objective optical system of Example 4 along with the paths of light rays that pass through the objective optical system.

The objective optical system of Example 4 corresponds to both of the first objective optical system and the second objective optical system described above, and is configured to satisfy all of Conditional Formulae (1) through (6). A cemented lens LS2 within a second lens group G2 of the objective optical system of Example 4 is the same as that of Example 1. That is, the cemented lens LS2 is formed by a fifth lens L5 having a positive refractive power and a sixth lens L6, which is a meniscus lens having a negative refractive power and a convex surface toward the image side, provided in this order from the object side.

Figure 13:
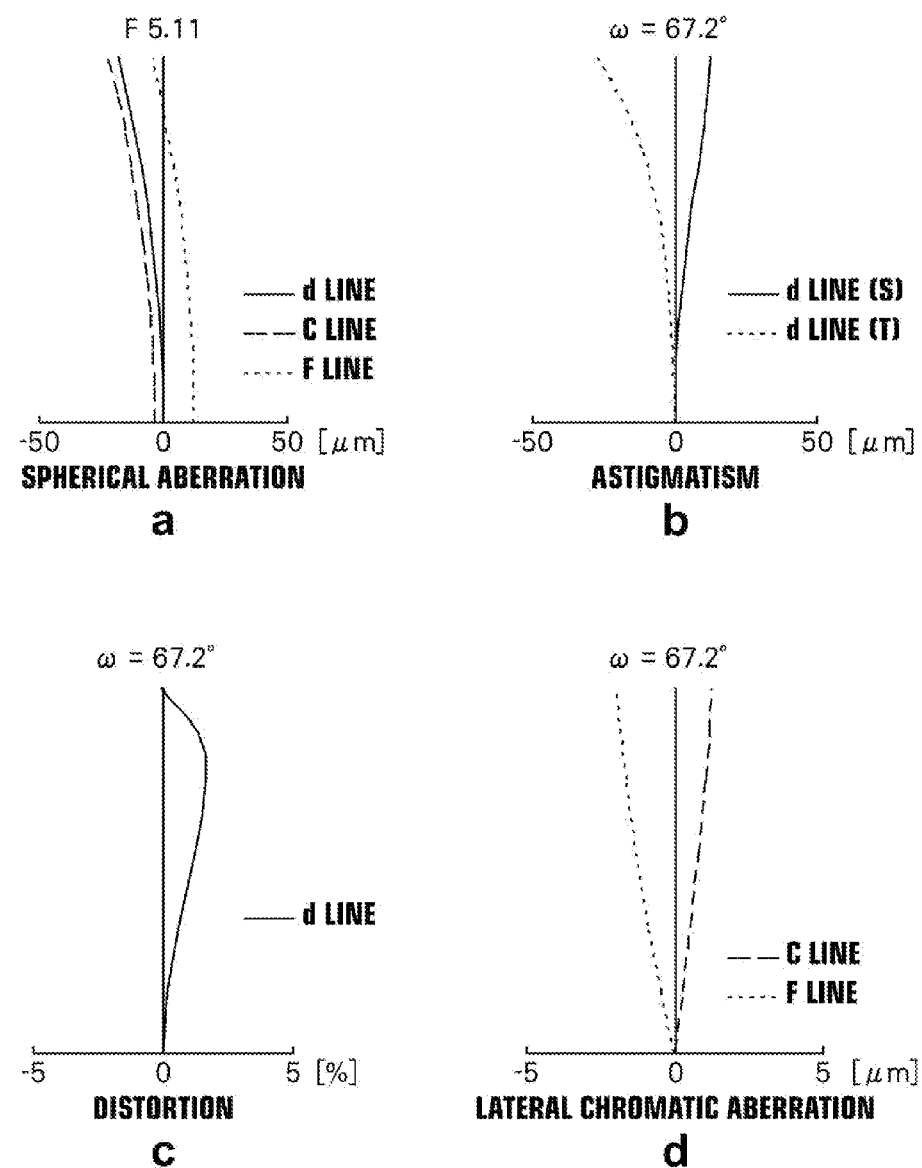
FIG. 13 is collection of diagrams that illustrate aberrations of the objective optical system of Example 4.

FIG. 13 is a collection of diagrams that illustrate aberrations of the objective optical system of Example 4.

Table 4 below shows lens data of the objective optical system of Example 4.

TABLE 4

Example 4: Lens Data

| Surface Number (i) | Radius of Curvature (Ri) | Distance (Di) | Ndj | vdj |
|---|---|---|---|---|
| 1 | 4.9998 | 0.25 | 1.88300 | 40.80 |
| 2 | 0.5800 | 0.44 | | |
| 3 | ∞ | 0.75 | 1.72825 | 28.50 |
| 4 | −0.6452 | 0.25 | 1.88300 | 40.80 |
| 5 | ∞ | 0.04 | | |
| 6 (Aperture Stop) | ∞ | 0.00 | | |
| 7 | ∞ | 0.73 | 1.51633 | 64.10 |
| 8 | −0.9127 | 0.10 | | |
| 9 | 2.3104 | 0.78 | 1.62041 | 60.30 |
| 10 | −0.7407 | 0.27 | 2.15400 | 17.20 |
| 11 | −1.2209 | 0.36 | | |
| 12 | ∞ | 2.00 | 1.55920 | 53.90 |
| 13 | ∞ | 0.15 | 1.51633 | 64.10 |
| 14 | ∞ | 0.00 | | |

As can be understood from the above lens data and the like, the angle of view of the objective optical system of Example 4 can be widened while suppressing the generation of lateral chromatic aberration.

Example 5

FIG. 6 is a sectional diagram that illustrates the schematic configuration of an objective optical system of Example 5 along with the paths of light rays that pass through the objective optical system.

The objective optical system of Example 5 corresponds to both of the first objective optical system and the second objective optical system described above, and is configured to satisfy all of Conditional Formulae (1) through (6). A cemented lens LS2 within a second lens group G2 of the objective optical system of Example 5 is the same as that of Example 1. That is, the cemented lens LS2 is formed by a fifth lens L5 having a positive refractive power and a sixth lens L6, which is a meniscus lens having a negative refractive power and a convex surface toward the image side, provided in this order from the object side.

FIG. 14 is a collection of diagrams that illustrate aberrations of the objective optical system of Example 5.

Table 5 below shows lens data of the objective optical system of Example 5.

TABLE 5

Example 5: Lens Data

| Surface Number (i) | Radius of Curvature (Ri) | Distance (Di) | Ndj | vdj |
|---|---|---|---|---|
| 1 | 4.9998 | 0.25 | 1.88300 | 40.80 |
| 2 | 0.5800 | 0.44 | | |
| 3 | ∞ | 0.75 | 1.72825 | 28.50 |
| 4 | −0.6452 | 0.25 | 1.88300 | 40.80 |
| 5 | ∞ | 0.04 | | |
| 6 (Aperture Stop) | ∞ | 0.00 | | |
| 7 | ∞ | 0.75 | 1.51633 | 64.10 |
| 8 | −0.9350 | 0.10 | | |
| 9 | 2.3735 | 0.78 | 1.62041 | 60.30 |
| 10 | −0.7407 | 0.27 | 1.94595 | 18.00 |
| 11 | −1.3308 | 0.34 | | |
| 12 | ∞ | 2.00 | 1.55920 | 53.90 |
| 13 | ∞ | 0.15 | 1.51633 | 64.10 |
| 14 | ∞ | 0.00 | | |

As can be understood from the above lens data and the like, the angle of view of the objective optical system of Example 5 can be widened while suppressing the generation of lateral chromatic aberration.

Example 6

FIG. 7 is a sectional diagram that illustrates the schematic configuration of an objective optical system of Example 6 along with the paths of light rays that pass through the objective optical system.

The objective optical system of Example 6 corresponds to both of the first objective optical system and the second objective optical system described above, and is configured to satisfy all of Conditional Formulae (1) through (6). A cemented lens LS2 within a second lens group G2 of the objective optical system of Example 6 is the same as that of Example 1. That is, the cemented lens LS2 is formed by a fifth lens L5 having a positive refractive power and a sixth lens L6, which is a meniscus lens having a negative refractive power and a convex surface toward the image side, provided in this order from the object side.

FIG. 15 is a collection of diagrams that illustrate aberrations of the objective optical system of Example 6.

Table 6 below shows lens data of the objective optical system of Example 6.

TABLE 6

Example 6: Lens Data

| Surface Number (i) | Radius of Curvature (Ri) | Distance (Di) | Ndj | vdj |
|---|---|---|---|---|
| 1 | 4.9998 | 0.25 | 1.88300 | 40.80 |
| 2 | 0.5800 | 0.44 | | |
| 3 | ∞ | 0.75 | 1.72825 | 28.50 |
| 4 | −0.6452 | 0.25 | 1.88300 | 40.80 |
| 5 | ∞ | 0.04 | | |
| 6 (Aperture Stop) | ∞ | 0.00 | | |
| 7 | ∞ | 0.73 | 1.51633 | 64.10 |
| 8 | −0.9258 | 0.12 | | |
| 9 | 2.4390 | 0.76 | 1.62041 | 60.30 |
| 10 | −0.7143 | 0.27 | 2.10205 | 16.80 |
| 11 | −1.1886 | 0.37 | | |
| 12 | ∞ | 2.00 | 1.55920 | 53.90 |
| 13 | ∞ | 0.15 | 1.51633 | 64.10 |
| 14 | ∞ | 0.00 | | |

As can be understood from the above lens data and the like, the angle of view of the objective optical system of Example 6 can be widened while suppressing the generation of lateral chromatic aberration.

Example 7

FIG. 8 is a sectional diagram that illustrates the schematic configuration of an objective optical system of Example 7 along with the paths of light rays that pass through the objective optical system.

The objective optical system of Example 7 corresponds to both of the first objective optical system and the second objective optical system described above, and is configured to satisfy all of Conditional Formulae (1) through (6). A cemented lens LS2 within a second lens group G2 of the objective optical system of Example 7 is the same as that of Example 1. That is, the cemented lens LS2 is formed by a fifth lens L5 having a positive refractive power and a sixth lens L6, which is a meniscus lens having a negative refractive power and a convex surface toward the image side, provided in this order from the object side.

Figure 16:
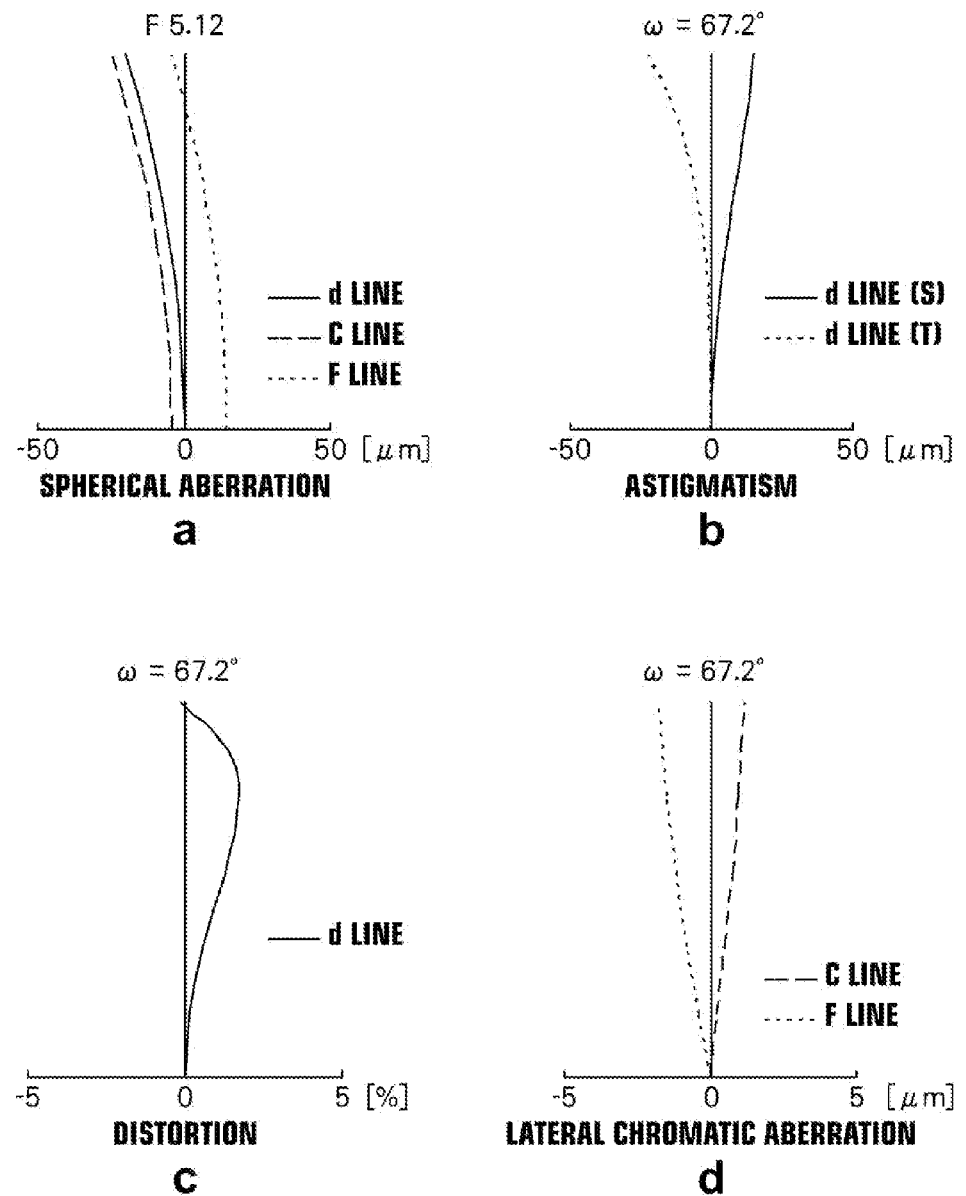
FIG. 16 is collection of diagrams that illustrate aberrations of the objective optical system of Example 7.

FIG. 16 is a collection of diagrams that illustrate aberrations of the objective optical system of Example 7.

Table 7 below shows lens data of the objective optical system of Example 7.

TABLE 7

Example 7: Lens Data

| Surface Number (i) | Radius of Curvature (Ri) | Distance (Di) | Ndj | vdj |
|---|---|---|---|---|
| 1 | 5.0988 | 0.25 | 1.88300 | 40.80 |
| 2 | 0.5800 | 0.44 | | |
| 3 | ∞ | 0.75 | 1.72825 | 28.50 |
| 4 | −0.6494 | 0.25 | 1.88300 | 40.80 |
| 5 | ∞ | 0.04 | | |
| 6 (Aperture Stop) | ∞ | 0.00 | | |
| 7 | ∞ | 0.73 | 1.51633 | 64.10 |
| 8 | −0.9072 | 0.10 | | |
| 9 | 2.4390 | 0.78 | 1.62041 | 60.30 |
| 10 | −0.7407 | 0.27 | 2.10205 | 16.80 |
| 11 | −1.2342 | 0.36 | | |
| 12 | ∞ | 2.00 | 1.55920 | 53.90 |
| 13 | ∞ | 0.15 | 1.51633 | 64.10 |
| 14 | ∞ | 0.00 | | |

As can be understood from the above lens data and the like, the angle of view of the objective optical system of Example 7 can be widened while suppressing the generation of lateral chromatic aberration.

Example 8

FIG. 9 is a sectional diagram that illustrates the schematic configuration of an objective optical system of Example 8 along with the paths of light rays that pass through the objective optical system.

The objective optical system of Example 8 corresponds to both of the first objective optical system and the second objective optical system described above, and is configured to satisfy all of Conditional Formulae (1) through (6). A cemented lens LS2 within a second lens group G2 of the objective optical system of Example 8 is the same as that of Example 1. That is, the cemented lens LS2 is formed by a fifth lens L5 having a positive refractive power and a sixth lens L6, which is a meniscus lens having a negative refractive power and a convex surface toward the image side, provided in this order from the object side.

Figure 17:
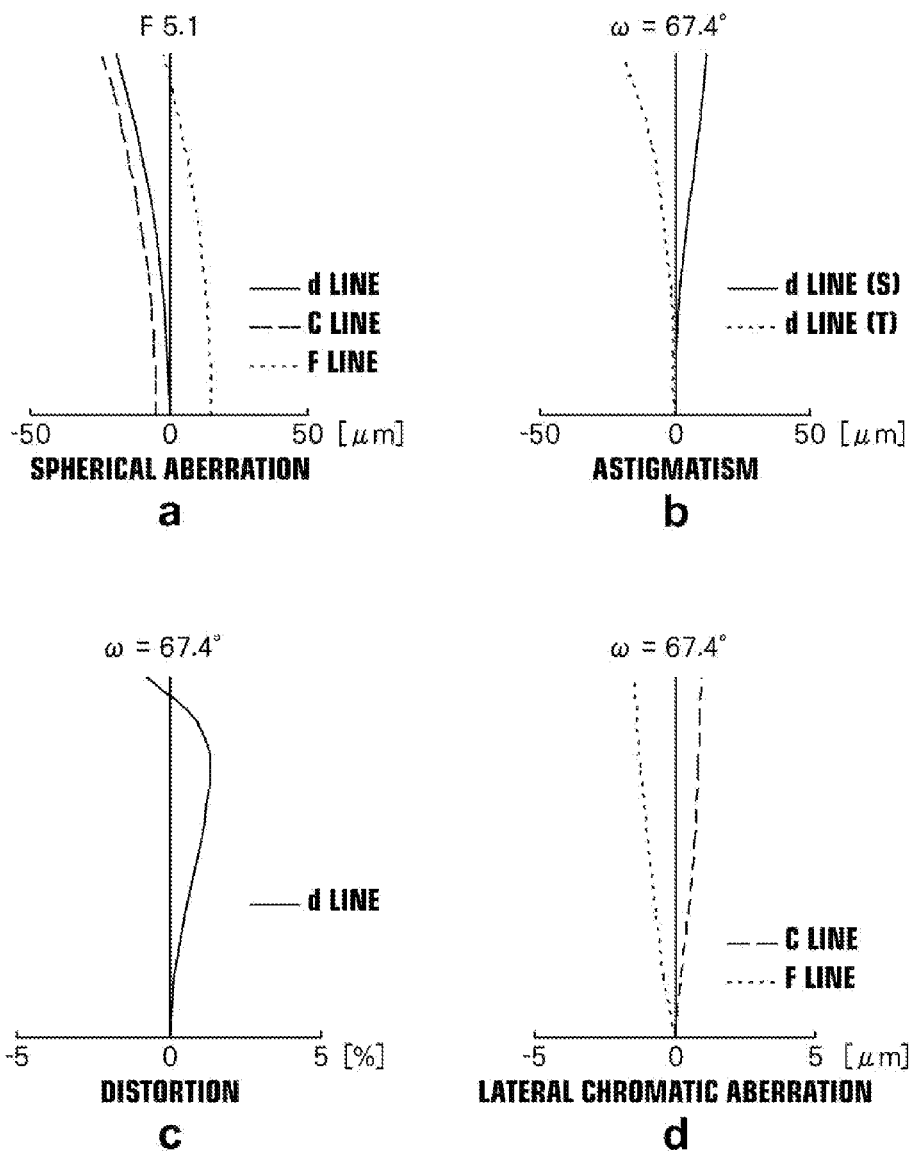
FIG. 17 is collection of diagrams that illustrate aberrations of the objective optical system of Example 8.

FIG. 17 is a collection of diagrams that illustrate aberrations of the objective optical system of Example 8.

Table 8 below shows lens data of the objective optical system of Example 8.

TABLE 8

Example 8: Lens Data

| Surface Number (i) | Radius of Curvature (Ri) | Distance (Di) | Ndj | vdj |
|---|---|---|---|---|
| 1 | 4.9998 | 0.25 | 1.88300 | 40.80 |
| 2 | 0.5556 | 0.44 | | |
| 3 | 8.4585 | 0.75 | 1.72825 | 28.50 |
| 4 | −0.6565 | 0.25 | 1.88300 | 40.80 |
| 5 | 5.6421 | 0.04 | | |
| 6 (Aperture Stop) | ∞ | 0.00 | | |
| 7 | 3.0775 | 0.73 | 1.51633 | 64.10 |
| 8 | −0.9789 | 0.12 | | |
| 9 | 2.4390 | 0.76 | 1.62041 | 60.30 |
| 10 | −0.7143 | 0.27 | 2.10205 | 16.80 |
| 11 | −1.1813 | 0.37 | | |
| 12 | ∞ | 2.00 | 1.55920 | 53.90 |
| 13 | ∞ | 0.15 | 1.51633 | 64.10 |
| 14 | ∞ | 0.00 | | |

As can be understood from the above lens data and the like, the angle of view of the objective optical system of Example 8 can be widened while suppressing the generation of lateral chromatic aberration.

Table 9 below shows values related to the conditional formulae as described above.

TABLE 9

| Conditional Formula | Equation within Conditional Formula | Values of Equations within Conditional Formulae | | | | | | | |
|---|---|---|---|---|---|---|---|---|---|
| | | Example 1 | Example 2 | Example 3 | Example 4 | Example 5 | Example 6 | Example 7 | Example 8 |
| (1) | vd (RN) | 17.5 | 17.5 | 16.8 | 17.2 | 18.0 | 16.8 | 16.8 | 16.8 |
| (2) | vd (RN)/(ng − nF) | 483.2 | 483.0 | 380.3 | 470.7 | 523.0 | 380.3 | 380.3 | 380.3 |
| (3) | vd (RP) + vd (RN) | 77.8 | 77.8 | 77.1 | 77.5 | 78.3 | 77.1 | 77.1 | 77.1 |
| (4) | vd (RP) − vd (RN) | 42.8 | 42.8 | 43.5 | 43.1 | 42.3 | 43.5 | 43.5 | 43.5 |
| (5) | f1/f | −1.31 | −1.31 | −1.3 | −1.31 | −1.31 | −1.32 | −1.31 | −1.24 |
| (6) | f2-6/f | 1.99 | 2.03 | 1.98 | 1.97 | 1.97 | 2 | 1.98 | 2.05 |

The present invention has been described with reference to the embodiments and Examples thereof. However, the present invention is not limited to the embodiments and Examples described above, and various modifications are possible. For example, the values of the radii of curvature of each lens component, the distances among surfaces, the refractive indices, the Abbe's numbers, etc., are not limited to the numerical values indicated in connection with the Examples, and may be other values.

What is claimed is:

1. An objective optical system, comprising:
    a first lens group having a negative refractive power;
    an aperture stop; and
    a second lens group having a positive refractive power, provided in this order from an object side;
    the first lens group comprising a negative single lens and a cemented lens formed by cementing a positive lens and a negative lens together, provided in this order from the object side;
    the second lens group comprising a positive single lens and a cemented lens formed by cementing a positive lens and a negative lens together, provided in this order from the object side; and
    the objective optical system satisfying Conditional Formulae (1) and (5b) below:

$$15.0 < vd(RN) < 18.6 \qquad (1)$$

$$-1.4 < f1/f < -1.2 \qquad (5b)$$

wherein vd(RN) is the Abbe's number of the negative lens in the cemented lens within the second lens group with respect to the d line, f1 is the focal length of the lens provided most toward the object side, and f is the focal length of the entire lens system.

2. An objective optical system as defined in claim 1 that satisfies Conditional Formula (1a) below:

$$16.0 < vd(RN) < 18.4 \qquad (1a).$$

3. An objective optical system as defined in claim 1 that satisfies Conditional Formula (1b) below:

$$16.5 \le vd(RN) < 18.2 \qquad (1b).$$

4. An objective optical system as defined in claim 1, wherein:
    the cemented lens within the first lens group is formed by a positive lens having a convex surface toward the image side, and a negative lens, provided in this order from the object side.

5. An objective optical system as defined in claim 1, wherein:
    the cemented lens within the second lens group is formed by a positive lens and a negative meniscus lens having a convex surface toward the image side, provided in this order from the object side.

6. An objective optical system as defined in claim 1, wherein:
    the cemented lens within the second lens group is formed by a negative lens and a positive lens having a convex surface toward the image side, provided in this order from the object side.

7. An objective optical system as defined in claim 1, which is employed as an objective optical system of an endoscope.

8. An endoscope comprising an objective optical system as defined in claim 1.

9. An objective optical system as defined in claim 1 that satisfies Conditional Formula (2) below:

$$380 \le vd(RN)/(ng-nF) < 1080 \qquad (2)$$

wherein vd(RN) is the Abbe's number of the negative lens in the cemented lens within the second lens group with respect to the d line, ng is the refractive index of the negative lens in the cemented lens within the second lens group with respect to the g line (435.84 nm), and nF is the refractive index of the negative lens in the cemented lens within the second lens group with respect to the F line (486.13 nm).

10. An objective optical system as defined in claim 9 that satisfies Conditional Formula (2a) below:

$$380 \le vd(RN)/(ng-nF) < 600 \qquad (2a).$$

11. An objective optical system as defined in claim 9 that satisfies Conditional Formula (2b) below:

$$380 \le vd(RN)/(ng-nF) < 525 \qquad (2b).$$

12. An objective optical system as defined in claim 1 that satisfies Conditional Formula (3) below:

$$vd(RP)+vd(RN) < 79 \qquad (3)$$

wherein vd(RP) is the Abbes number of the positive lens in the cemented lens within the second lens group with respect to the d line, and vd(RN) is the Abbes number of the negative lens in the cemented lens within the second lens group with respect to the d line.

13. An objective optical system as defined in claim 12 that satisfies Conditional Formula (3a) below:

$$70 < vd(RP)+vd(RN) < 78.8 \qquad (3a).$$

14. An objective optical system as defined in claim 12 that satisfies Conditional Formula (3b) below:

$$75 < vd(RP)+vd(RN) < 78.5 \qquad (3b).$$

15. An objective optical system as defined in claim 1 that satisfies Conditional Formula (4) below:

$$41.5 < vd(RP)-vd(RN) \qquad (4)$$

wherein vd(RP) is the Abbes number of the positive lens in the cemented lens within the second lens group with respect to the d line, and vd(RN) is the Abbes number of the negative lens in the cemented lens within the second lens group with respect to the d line.

16. An objective optical system as defined in claim 15 that satisfies Conditional Formula (4a) below:

$$41.8 < vd(RP) - vd(RN) < 45.0 \qquad (4a).$$

17. An objective optical system as defined in claim 15 that satisfies Conditional Formula (4b) below:

$$42.0 < vd(RP) - vd(RN) < 44.0 \qquad (4b).$$

18. An objective optical system as defined in claim 1 that satisfies Conditional Formula (6) below:

$$\mathbf{1.92} < f2\text{-}6/f < 3 \qquad (6)$$

wherein f2–6 is the combined focal length of the lenses other than the lens provided most toward the object side, and f is the focal length of the entire lens system.

19. An objective optical system as defined in claim 18 that satisfies Conditional Formula (6a) below:

$$1.92 < f2\text{-}6/f < 2.5 \qquad (6a).$$

20. An objective optical system as defined in claim 18 that satisfies Conditional Formula (6b) below:

$$1.92 < f2\text{-}6/f < 2.2 \qquad (6b).$$

* * * * *